US011602326B2

(12) United States Patent
Cho

(10) Patent No.: US 11,602,326 B2
(45) Date of Patent: Mar. 14, 2023

(54) ULTRASONIC DIAGNOSTIC APPARATUS

(71) Applicant: Samsung Medison Co., Ltd., Gangwon-do (KR)

(72) Inventor: Joo Yeon Cho, Chuncheon-si (KR)

(73) Assignee: SAMSUNG MEDISON CO., LTD., Gangwon-Do (KR)

( * ) Notice: Subject to any disclaimer, the term of this patent is extended or adjusted under 35 U.S.C. 154(b) by 586 days.

(21) Appl. No.: 16/294,007

(22) Filed: Mar. 6, 2019

(65) Prior Publication Data

US 2019/0274660 A1 Sep. 12, 2019

(30) Foreign Application Priority Data

Mar. 7, 2018 (KR) .......................... 10-2018-0026836

(51) Int. Cl.
*A61B 8/00* (2006.01)
*H02N 2/10* (2006.01)
*F16M 11/10* (2006.01)
*A61B 17/00* (2006.01)

(52) U.S. Cl.
CPC .............. *A61B 8/44* (2013.01); *A61B 8/4209* (2013.01); *A61B 8/462* (2013.01); *A61B 8/467* (2013.01); *F16M 11/10* (2013.01); *H02N 2/10* (2013.01); *A61B 8/4405* (2013.01); *A61B 2017/00398* (2013.01); *A61B 2560/0431* (2013.01)

(58) Field of Classification Search
USPC ......................................................... 600/437
See application file for complete search history.

(56) References Cited

U.S. PATENT DOCUMENTS 8,161,815 B2    4/2012  Naruse
2003/0223188 A1  12/2003  Ha et al.
(Continued)

FOREIGN PATENT DOCUMENTS

EP       1790900 A2 *   5/2007   ............ F16M 11/10
EP     1 977 693 A1    10/2008
(Continued)

OTHER PUBLICATIONS

English Translation of KR-20100081427-A (Year: 2010).*
Extended Search Report issued in European Application No. 19157817. 8, dated Apr. 26, 2019.

*Primary Examiner* — Jason M Ip
*Assistant Examiner* — Renee C Langhals
(74) *Attorney, Agent, or Firm* — Morgan, Lewis & Bockius LLP

(57) ABSTRACT

Disclosed is an ultrasonic diagnostic apparatus including an improved actuator to compensate for a weight of an input/output device. The ultrasonic diagnostic apparatus includes a main body, an input/output device coupled to the main body and configured to receive information from a user or output information received from the main body, and a connection device to connect the main body and the input/output device, wherein the connection device includes a shaft having a shaft body, a link frame having a frame body and a shaft coupling portion extending from the frame body to be coupled with the shaft, and an actuator including a torsion spring having a first end supported by the shaft and a second end supported by the link frame, so as to compensate for a weight of the input/output device.

15 Claims, 11 Drawing Sheets

(56) References Cited

U.S. PATENT DOCUMENTS

| | | | |
|---|---|---|---|
| 2004/0245419 A1* | 12/2004 | Sweere | F16M 11/2064 |
| | | | 248/276.1 |
| 2005/0002159 A1 | 1/2005 | Jeong | |
| 2007/0023598 A1* | 2/2007 | Kim | A61B 90/50 |
| | | | 248/276.1 |
| 2008/0249406 A1* | 10/2008 | Naruse | A61B 8/00 |
| | | | 600/437 |
| 2009/0166501 A1 | 7/2009 | Wang et al. | |
| 2010/0079932 A1 | 4/2010 | Zhou | |
| 2012/0310256 A1* | 12/2012 | Brisson | A61B 34/77 |
| | | | 606/130 |
| 2016/0181951 A1 | 6/2016 | Qiu et al. | |
| 2017/0300083 A1* | 10/2017 | Park | F16M 11/24 |

FOREIGN PATENT DOCUMENTS

| | | | |
|---|---|---|---|
| KR | 100576748 B1 * | 5/2006 | |
| KR | 10-2009-0077571 A | 7/2009 | |
| KR | 20100081427 A * | 7/2010 | |
| KR | 10-2014-0063995 A | 5/2014 | |

* cited by examiner

ULTRASONIC DIAGNOSTIC APPARATUS

CROSS-REFERENCE TO RELATED APPLICATION(S)

This application is based on and claims priority under 35 U.S.C. § 119 to Korean Patent Application No. 10-2018-0026836, filed on Mar. 7, 2018 in the Korean Intellectual Property Office, the disclosure of which is incorporated by reference herein in its entirety.

BACKGROUND

1. Technical Field

The present disclosure relates to an ultrasonic diagnostic apparatus, and more particularly, to an ultrasonic diagnostic apparatus including an improved actuator for compensating for the weight of an input/output device.

2. Description of the Related Art

An ultrasonic diagnostic apparatus is an apparatus that irradiates an ultrasonic signal from a body surface of a target toward a target site in the body and obtains an image of a monolayer or blood flow of soft tissues without invasion by using information of a reflected ultrasonic signal (ultrasonic echo signal).

The ultrasonic diagnostic apparatus is small, inexpensive, real-time displayable, easy to use, and has a high level of safety because there is no radiation exposure, compared to other imaging apparatuses such as an X-ray diagnostic apparatus, an X-ray CT scanner, an MRI (Magnetic Resonance Image) and a nuclear medicine diagnostic apparatus.

Accordingly, the ultrasonic diagnostic apparatus is widely used for the diagnosis of the heart, abdomen, urinary system and in the field of obstetrics.

The ultrasonic diagnostic apparatus may include a main body, a display disposed on an upper portion of the main body and displaying a diagnostic result obtained through the received ultrasound as an image, and a control panel disposed at the front of the display to allow a user to operate the ultrasonic diagnostic apparatus.

The control panel and the display may correspond to an input/output device for inputting or outputting information. For ease of diagnosis of the user using the ultrasonic diagnostic apparatus, the input/output device should be movable.

Accordingly, the ultrasonic diagnostic apparatus may include an actuator that compensates for a weight of the input/output device so that the user may smoothly move the input/output device.

In general, the actuator may include a gas spring, a tension spring, or a compression spring. The actuator including the gas spring may have different acting forces depending on the temperature expansion or contraction of gas and liquid, and defects may occur due to gas leakage when a high-pressure cylinder is used for a long period of time.

Since the actuator including the compression spring uses a separate wire, disconnection of the wire may be caused. The actuator including the tension spring may be insufficient to realize a slim design because of its complicated structure.

In addition, since the actuator including the gas spring, the tension spring, or the compression spring should be disposed at a central portion of a connection device connecting the main body and the input/output device, the arrangement of a cable provided inside the connection device may be hindered.

SUMMARY

It is an aspect of the present disclosure to provide an ultrasonic diagnostic apparatus including an improved actuator to compensate for a weight of an input/output device so that a user may smoothly move the input/output device.

It is another aspect of the present disclosure to provide an ultrasonic diagnostic apparatus including an improved actuator including a torsion spring.

It is another aspect of the present disclosure to provide an ultrasonic diagnostic apparatus including an improved actuator to exert the same rotational force regardless of a rotational angle of a connecting device.

Additional aspects of the present disclosure will be set forth in part in the description which follows and, in part, will be obvious from the description, or may be learned by practice of the present disclosure.

In accordance with an aspect of the present disclosure, an ultrasonic diagnostic apparatus may include a main body, an input/output device coupled to the main body and configured to receive information from a user or output information received from the main body, and a connection device to connect the main body and the input/output device, wherein the connection device may include a shaft having a shaft body, a link frame having a frame body and a shaft coupling portion extending from the frame body to be coupled with the shaft, and an actuator including a torsion spring having a first end supported by the shaft and a second end supported by the link frame, so as to compensate for a weight of the input/output device.

The link frame may include a first link frame and a second link frame adjacent to the first link frame, and the first end may be supported by the shaft passing through the first link frame and the second end may be supported by the second link frame.

The actuator may be configured to be rotated together with the link frame.

The actuator may be configured to exert the same rotational force irrespective of a rotation angle of the link frame.

The shaft may include a first coupling portion provided to be engaged with the link frame and rotated together with the link frame, and the link frame may include a second coupling portion provided to be engaged with the first coupling portion.

The actuator may include a third coupling portion provided to be engaged with the shaft and rotated together with the shaft, and the shaft may include a fourth coupling portion provided to be engaged with the third coupling portion.

The first coupling portion may include a protrusion protruding from the shaft body.

The shaft coupling portion may include a coupling portion body and a through portion provided on the coupling portion body to insert the shaft body, and the second coupling portion may include a hole extending from the through portion.

The fourth coupling portion may include a first supporting portion extending from the shaft body to support the actuator, and a groove provided on the first supporting portion to receive the third coupling portion.

The link frame may further include a second supporting portion provided on the frame body to support the second end.

The second supporting portion may support the second end and a portion between the first end and the second end according to the rotation of the link frame.

The second supporting portion may include a roller provided to roll along the actuator by the rotation of the link frame.

A plurality of the actuators may be provided, and the plurality of actuators may be disposed at opposite end portions of the shaft, respectively.

A plurality of the shafts, the shaft coupling portions, and the actuators may be provided, and the plurality of actuators may be disposed on the plurality of respective shafts inserted into two of the respective shaft coupling portions facing each other among the plurality of shaft coupling portions.

A plurality of the shafts and the shaft coupling portions may be provided, and the plurality of shafts may be disposed on the plurality of shaft coupling portions, respectively.

In accordance with another aspect of the present disclosure, an ultrasonic diagnostic apparatus may include a main body, an input/output device coupled to the main body and configured to receive information from a user or output information received from the main body, and a connection device to connect the main body and the input/output device, wherein the connection device includes a link frame provided to be rotatable, a shaft coupled with one end portion of the link frame to be rotated together with the link frame, and an actuator configured to compensate for a weight of the input/output device and rotate together with the link frame and the shaft.

The actuator may include a torsion spring having a first end supported by the shaft and a second end supported by the link frame.

The link frame may include a first link frame and a second link frame adjacent to the first link frame, and the first end may be supported by the shaft passing through the first link frame and the second end is supported by the second link frame.

In accordance with another aspect of the present disclosure, an ultrasonic diagnostic apparatus may include a main body, a control panel coupled to the main body and configured to receive information from a user, a display coupled to the control panel and configured to output information received from the main body, and an arm to connect the control panel and the display, wherein the arm includes, a link frame including a first link frame provided to be rotatable and a second link frame adjacent to the first link frame, a shaft inserted into the link frame, and an actuator having a first end supported by the shaft passing through the first link frame and a second end supported by the second link frame, so as to exert the same rotational force irrespective of a rotation angle of the link frame.

The actuator may include a torsion spring configured to be rotated together with the shaft.

BRIEF DESCRIPTION OF THE DRAWINGS

These and/or other aspects of the present disclosure will become apparent and more readily appreciated from the following description of the embodiments, taken in conjunction with the accompanying drawings of which.

DETAILED DESCRIPTION

Figure 1:
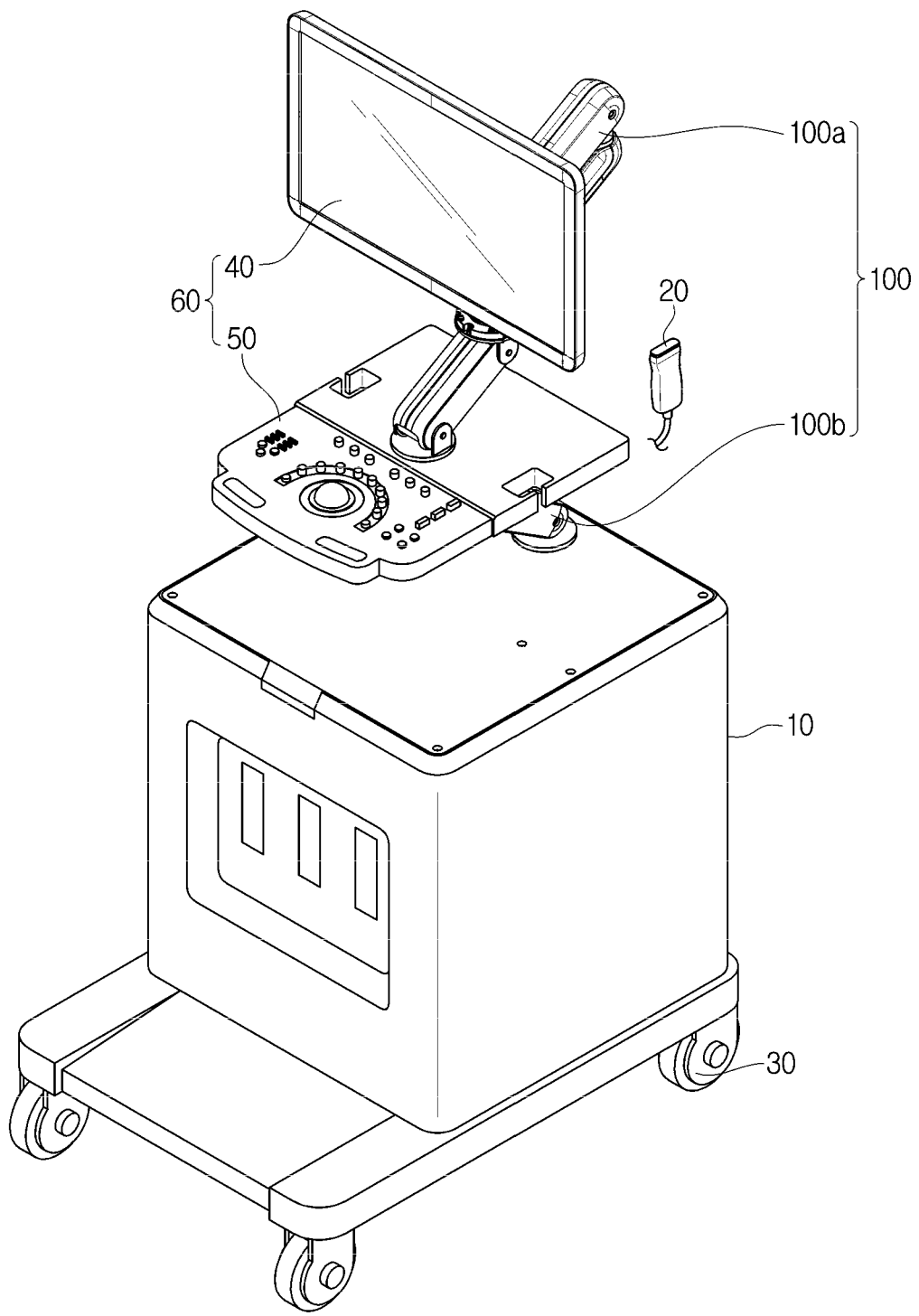
FIG. 1 is a perspective view illustrating an appearance of an ultrasonic diagnostic apparatus according to the present disclosure.

The embodiments described herein and the configurations shown in the drawings are only examples of preferred embodiments of the present disclosure, and various modifications may be made at the time of filing of the present disclosure to replace the embodiments and drawings of the present application.

Like reference numbers or designations in the various drawings of the present application represent parts or components that perform substantially the same functions.

The terms used in this specification are for the purpose of describing the embodiments and are not intended to restrict and/or to limit the disclosure. The singular expressions may include plural expressions, unless the context clearly dictates otherwise.

In this specification, the terms "comprises" and "has" are intended to indicate that there are features, numbers, steps, operations, elements, parts, or combinations thereof described in the specification, and do not exclude the presence or addition of one or more other features, numbers, steps, operations, elements, parts, or combinations thereof.

It will be understood that, although the terms first, second, etc. may be used herein to describe various components, these components should not be limited by these terms. These terms are only used to distinguish one component from another.

For example, without departing from the scope of the present disclosure, the first component may be referred to as a second component, and similarly, the second component may also be referred to as a first component.

In this specification, the terms "front," "rear," "upper," "lower," "left," and "right" are defined with reference to the drawings, and the shape and position of each component are not limited by these terms.

Hereinafter, embodiments according to the present disclosure will be described in detail with reference to the accompanying drawings.

Figure 2:
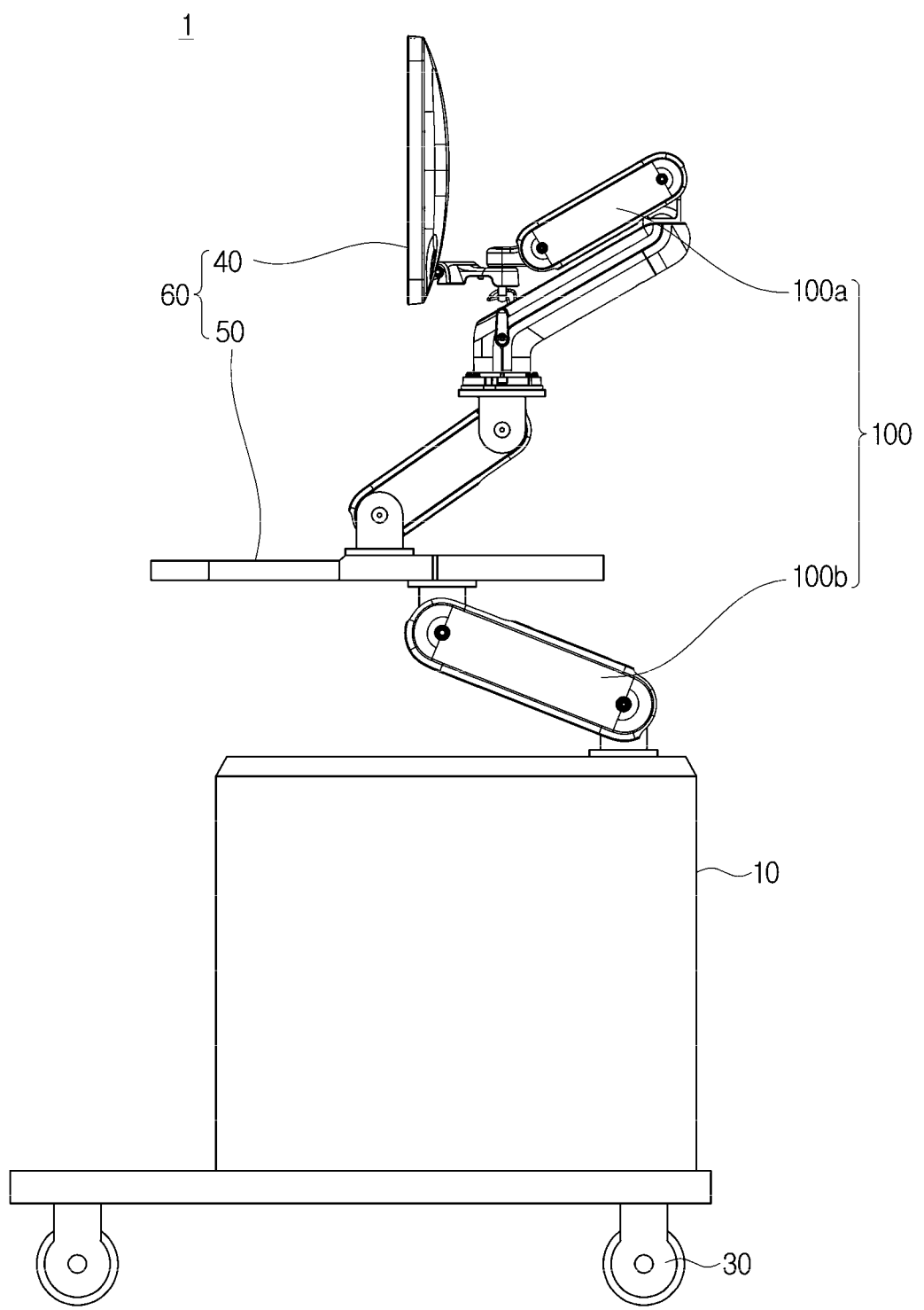
FIG. 2 is a view illustrating an appearance of a side of an ultrasonic diagnostic apparatus according to the present disclosure.

FIG. 1 is a perspective view illustrating an appearance of an ultrasonic diagnostic apparatus according to the present disclosure, and FIG. 2 is a view illustrating an appearance of a side of an ultrasonic diagnostic apparatus according to the present disclosure.

As illustrated in FIGS. 1 and 2, an ultrasonic diagnostic apparatus 1 may include a main body 10, and a probe 20 for transmitting an ultrasonic signal to an object to be diagnosed and receiving a signal reflected from the object.

The probe 20 may be connected to the main body 10 through a wireless or wired communication network to receive various signals required for controlling the probe 20 or to transmit an analog signal or a digital signal corresponding to the echo ultrasonic signal received by the probe 20.

The wireless communication network refers to a communication network capable of transmitting and receiving signals wirelessly and the main body 10 may perform wireless communication with the probe 20 through at least one of a short-range communication module and a mobile communication module.

The short-range communication module may refer to a module for short-range communication within a predetermined distance.

For example, the short-range communication technology may include wireless LAN, Wi-Fi, Bluetooth, Zigbee, Wi-Fi Direct (WFD), Ultra-Wideband (UWB), Infrared Data Association (IrDA), Bluetooth Low Energy (BLE), Near Field Communication (NFC), and the like.

The mobile communication module may transmit and receive a wireless signal with at least one of a base station, an external terminal, and a server on a mobile communication network. Herein, the wireless signal may refer to a signal including various types of data.

That is, the main body 10 may exchange signals including various types of data with the probe 20 via at least one of a base station and a server.

For example, the main body 10 may exchange signals including various types of data with the probe 20 via a base station using a mobile communication network such as 3G and 4G.

The main body 10 may exchange data with a hospital server connected through a Picture Archiving and Communication System (PACS) or other medical devices in the hospital.

The main body 10 may exchange data according to the DICOM (Digital Imaging and Communications in Medicine) standard, but is not limited thereto.

The main body 10 may exchange data with the probe 20 through a wired communication network. The wired communication network may refer to a communication network capable of sending and receiving signals to and from a wired network.

The main body 10 may exchange various signals with the probe 20 using a wired communication network such as a Peripheral Component Interconnect (PCI), a PCI-express, and a Universe Serial Bus (USB), but is not limited thereto.

The ultrasonic diagnostic apparatus 1 may include a display 40 disposed at an upper portion of the main body 10 for outputting a result obtained through the received ultrasonic signal as an image, and a control panel 50 for inputting various commands for allowing the user to operate the ultrasonic diagnostic apparatus 1.

An application relating to the operation of the ultrasonic diagnostic apparatus 1 may be displayed on the display 40. For example, ultrasonic images obtained in the ultrasonic diagnostic process or items relating to the operation of the ultrasonic diagnostic apparatus 1 may be displayed on the display 40.

When a plurality of the displays 40 are provided, the displays 40 may include a main display and an auxiliary display. For example, ultrasonic images obtained in the ultrasonic diagnostic process may be displayed on the main display, and items relating to the operation of the ultrasonic diagnostic apparatus 1 may be displayed on the auxiliary display.

The control panel 50 may receive not only the setting information relating to the probe 20 from the user but also various control commands for controlling the various ultrasonic diagnostic apparatuses 1 and the like.

The setting information relating to the probe 20 includes gain information, zoom information, focus information, TGC (Time Gain Compensation) information, depth information, frequency information, power information, frame average information, dynamic range information, and the like.

However, the setting information relating to the probe 20 is not limited to this embodiment, and may include information of various items that may be set for photographing an ultrasonic image. The information may be transmitted to the probe 20 through a wireless communication network or a wired communication network, and the probe 20 may be set according to the received information.

The main body 10 may receive various control commands such as an ultrasonic signal transmission command from the user through the control panel 50 or the display 40 and may transmit the control commands to the probe 20.

The display 40 may be implemented in various known ways such as a cathode ray tube (CRT), a liquid crystal display (LCD), a light emitting diode (LED), a plasma display panel (PDP), and an organic light emitting diode (OLED), but is not limited thereto.

The display 40 may display an ultrasonic image of a target site within the object. The ultrasonic image displayed on the display 40 may be a 2D ultrasonic image or a 3D ultrasonic image and various ultrasonic images may be displayed according to the operation modes of the ultrasonic diagnostic apparatus 1.

The display 40 may display not only menus and information items necessary for the ultrasonic diagnosis but also information on the operation state of the probe 20 and the like.

The ultrasonic image includes not only an amplitude-mode (A-mode) image, a brightness mode (B-mode) image, and a motion mode (M-mode) image, but also a color-mode (C-mode) image and a Doppler-mode (D-mode) image.

The A-mode image may refer to an ultrasonic image representing the size of the ultrasonic signal corresponding to an echo ultrasonic signal, the B-mode image may refer to an ultrasonic image in which the size of the ultrasonic signal corresponding to an echo ultrasonic signal is represented by brightness, and the M-mode image may refer to an ultrasonic image that indicates the movement of the object over time at a specific location.

The D-mode image may refer to an ultrasonic image in which a moving object is represented in a waveform using the Doppler effect, and the C-mode image may refer to an ultrasonic image in which a moving object is represented in a color spectrum form.

Meanwhile, when the display 40 is implemented as a touch screen type, the display 40 may also perform the function of the control panel 50. That is, the main body 10 may receive various commands from the user through at least one of the display 40 and the control panel 50.

The control panel 50 may be provided in the form of a keyboard, a foot switch, a foot pedal, or the like. When the control panel 50 is a keyboard, the control panel 50 may be provided on an upper portion of the main body 10. When the control panel 50 is a foot switch or a foot pedal, the control panel 50 may be provided on a lower portion of the main body 10.

For example, the keyboard may be implemented as hardware. Such keyboard may include at least one of a switch, a key, a joystick, and a trackball. As another example, the keyboard may be implemented as software, such as a graphical user interface. In this case, the keyboard may be displayed through the display 40.

In addition, although not shown in the drawings, the main body 10 may be provided with a voice recognition sensor to receive a voice command from the user.

The display 40 and the control panel 50 may be defined as an input/output device 60 by being combined together in that the display 40 and the control panel 50 receive information from the user or transmit information to the user.

The main body 10 may be provided with a moving device 30 to move the ultrasonic diagnostic apparatus 1. The moving device 30 may be a plurality of castors provided on a bottom surface of the main body 10.

The plurality of castors may be aligned to allow the main body 10 to run in a specific direction, may be arranged to be freely movable in any direction, or may be locked to stop at a specific position.

The ultrasonic diagnostic apparatus 1 may include a connection device 100 for connecting the control panel 50 or the display 40 to the main body 10. The connection device 100 may include an arm 100*a* for connecting the display 40 and the control panel 50, and a lift 100*b* for connecting the control panel 50 and the main body 10. The arm 100*a* may rotate or move the display 40.

The arm 100*a* constituting the connection device 100 will be described below but the explanation of the arm 100*a* may be applied to the lift 100*b* constituting the connecting device 100 as well.

Figure 3:
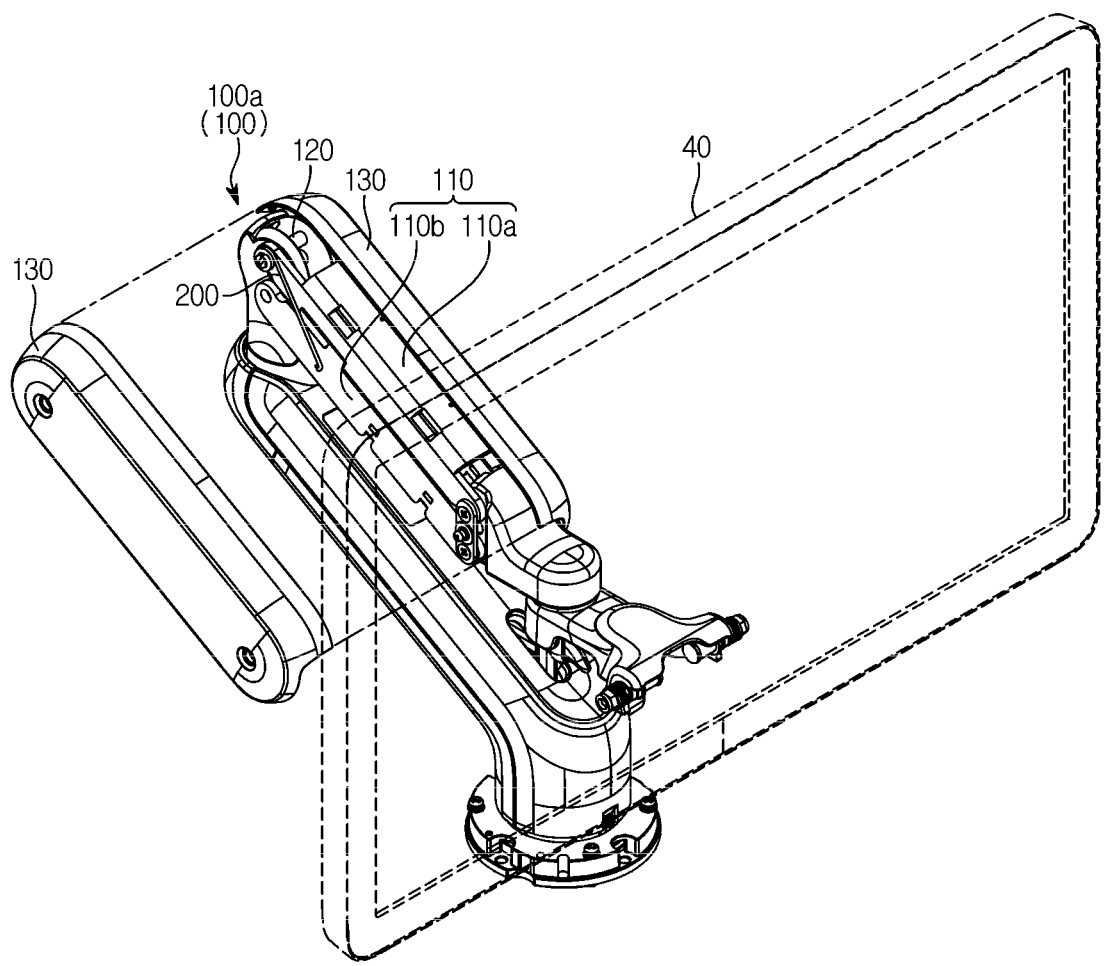
FIG. 3 is a perspective view illustrating the inside of a connection device in an ultrasonic diagnostic apparatus according to an embodiment of the present disclosure.
Figure 4:
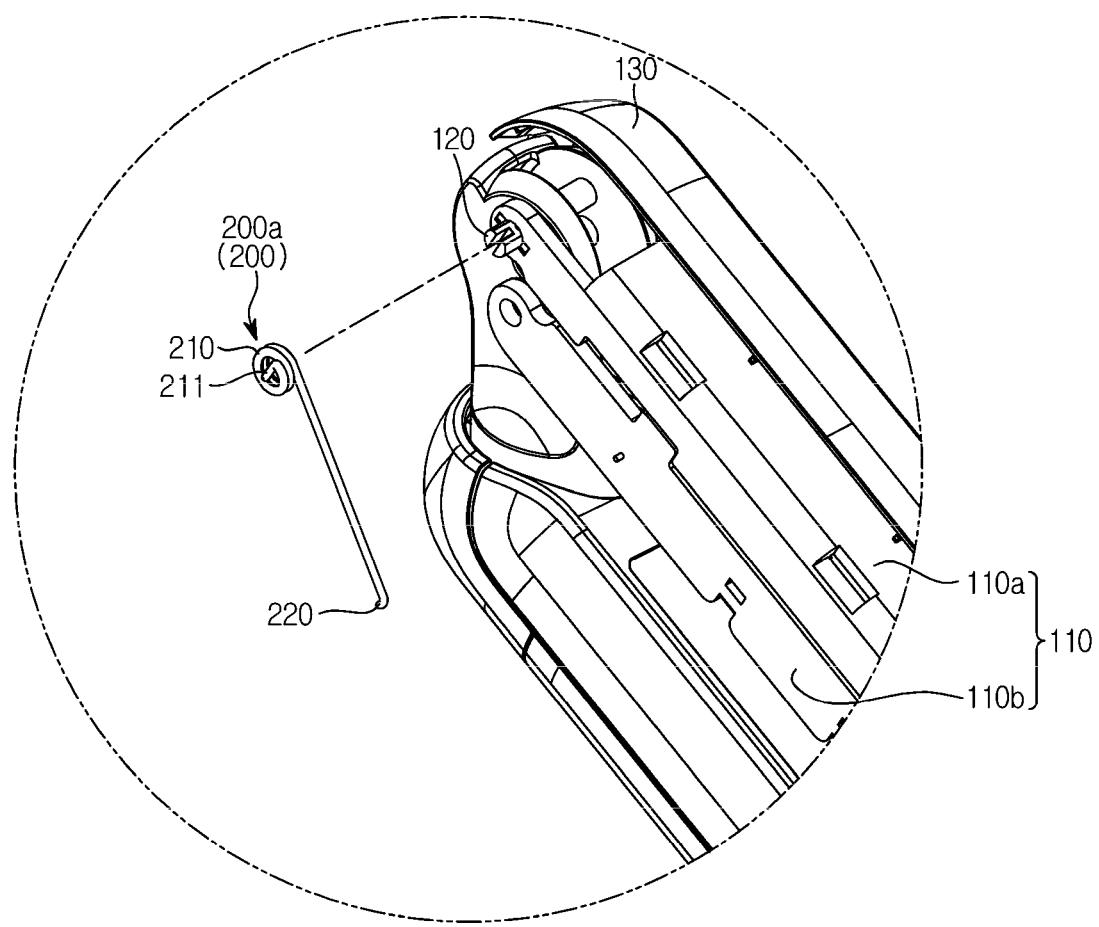
FIG. 4 is a perspective view illustrating the inside of a connection device in which an actuator is detached in an ultrasonic diagnostic apparatus according to an embodiment of the present disclosure.
Figure 5:
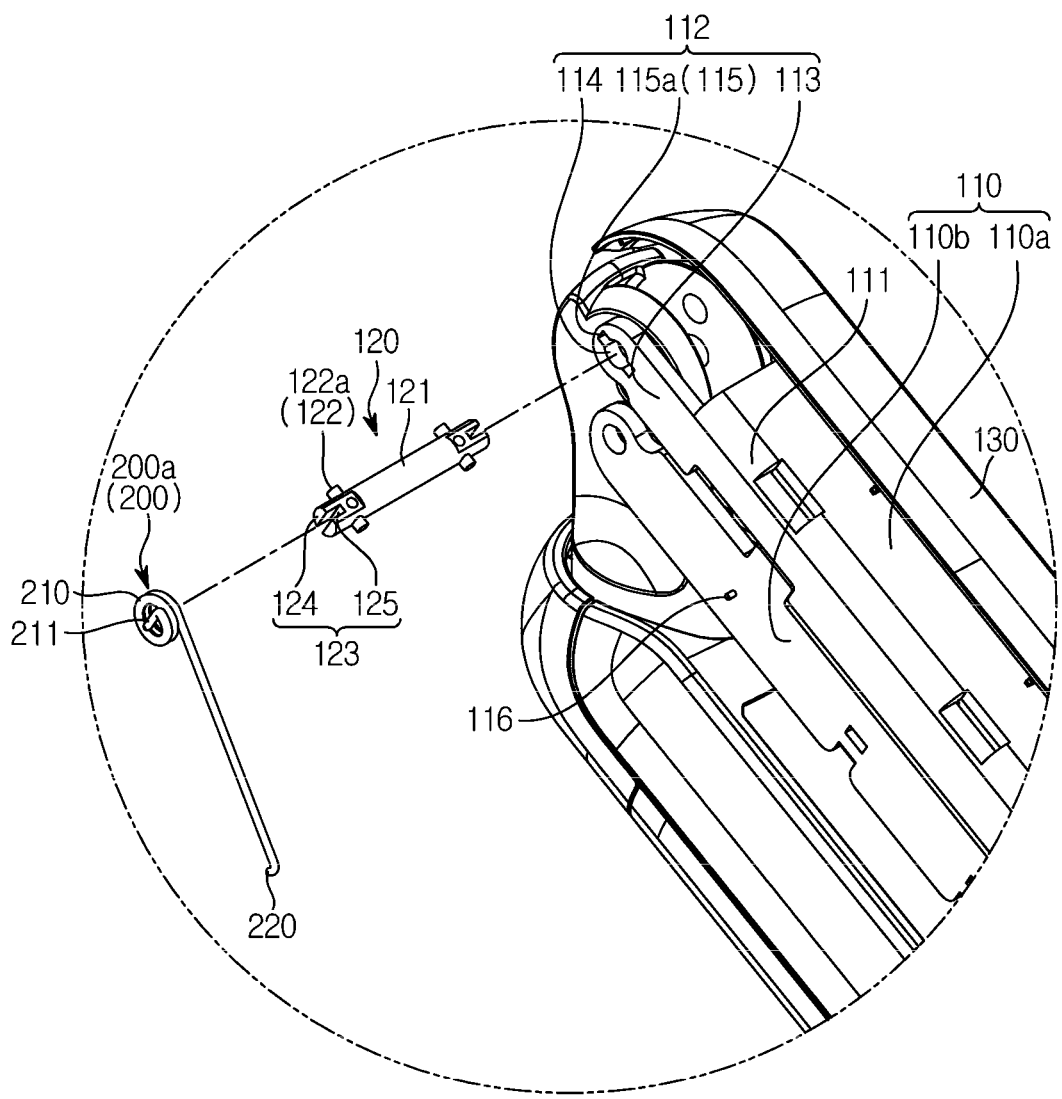
FIG. 5 is a perspective view illustrating the inside of a connection device in which an actuator and a shaft are detached in an ultrasonic diagnostic apparatus according to an embodiment of the present disclosure.

FIG. 3 is a perspective view illustrating the inside of a connection device in an ultrasonic diagnostic apparatus according to an embodiment of the present disclosure, FIG. 4 is a perspective view illustrating the inside of a connection device in which an actuator is detached in an ultrasonic diagnostic apparatus according to an embodiment of the present disclosure, and FIG. 5 is a perspective view illustrating the inside of a connection device in which an actuator and a shaft are detached in an ultrasonic diagnostic apparatus according to an embodiment of the present disclosure.

As illustrated in FIGS. 3 to 5, the connection device 100 according to an embodiment of the present disclosure may include a link frame 110 provided to be rotatable and a cover 130 provided to cover the link frame 110.

A plurality of the covers 130 may be provided and be detachably configured to cover opposite sides of the link frame 110. However, the present disclosure is not limited thereto.

The link frame 110 may include a first link frame 110*a* and a second link frame 110*b* adjacent to the first link frame 110*a*. The second link frame 110*b* may be disposed below the first link frame 110*a*, but is not limited thereto.

The connection device 100 may include a shaft 120 provided to be coupled to one end portion of the link frame 110. The link frame 110 may be configured to rotate about the shaft 120. The shaft 120 may constitute a rotation axis of the link frame 110.

The connection device 100 may include an actuator 200 configured to compensate for a weight of the input/output device 60 (refer to FIG. 1) including the display 40.

The input/output device 60 may generate a load on the connection device 100 by the weight of the input/output device 60, and thus the actuator 200 may be configured to generate a supporting force for compensating for the weight.

The actuator 200 may perform a function of supporting the load of the input/output device 60 and may also perform a buffering action for absorbing impact transmitted to the input/output device 60 and a function of fixing the position of the input/output device 60.

The actuator 200 may include an automatic actuator including a driving member (not shown) configured to automatically move the input/output device 60 by the user, and a manual actuator configured to manually move the input/output device 60 by the user.

Hereinafter, the actuator 200 according to the present invention will be described with reference to the manual actuator.

The actuator 200 may include a gas spring. The gas spring may refer to an element that performs a spring function by utilizing the elasticity of a gas (air or nitrogen) charged in a closed space.

The gas spring may have a feature of varying the air pressure so that the stroke of the spring may be kept constant regardless of an increase or decrease of the load. Since the gas spring uses gas inside a piston, the gas spring may be affected by the ambient temperature due to the characteristics of the gas.

For example, assuming an average temperature of 20° C. in Korea, when the ultrasonic diagnostic apparatus 1 produced in Korea is moved to an equatorial region where the external temperature is 50° C., the supporting force generated by the gas spring may be increased due to the external temperature.

Accordingly, in this case, when the ultrasonic diagnostic apparatus 1 produced in accordance with the temperature of Korea is moved to a hot region, the supporting force generated by the gas spring becomes large, so that the input/output device 60 may be moved too easily, contrary to the user's intention.

When the input/output device 60 is to be moved upward in this state, not only the input/output device 60 but also the main body 10 (refer to FIG. 1) of the ultrasonic diagnostic apparatus 1 may be moved up together.

On the contrary, when the ultrasonic diagnostic apparatus 1 is moved to a region where the temperature falls below zero, such as the Antarctic or the Arctic, the supporting force generated by the gas spring may converge to almost zero.

Accordingly, in this case, since the supporting force generated by the gas spring may not compensate for the weight of the input/output device 60, the user may need a great deal of force to move the input/output device 60.

Therefore, due to the characteristics of the gas spring, when the ultrasonic diagnostic apparatus 1 produced based on the temperature of Korea is moved to another region, the supporting force generated by the gas spring may be changed, so that it may be difficult for the user to move the input/output device 60.

The actuator 200 may also include a compression spring or a tension spring. The compression spring may cause disconnection of a wire due to interference with the wire (not shown) provided inside the connection device 100.

The actuator 200 including the tension spring may be insufficient to realize a slim design because of its complicated structure.

Since the actuator 200 including the gas spring, the tension spring, or the compression spring should be disposed at a central portion of the inside of the connection device 100 that connects the main body 10 and the input/output device 60, the arrangement of a cable (not shown) provided inside the connection device 100 may be hindered.

The actuator 200 according to the present disclosure may include a torsion spring 200a. The actuator 200 may generate a supporting force capable of compensating for the weight of the input/output device 60 through a simple structure using the torsion spring 200a.

The supporting force may be maintained by mounting the torsion spring 200a on the shaft 120 which is the rotation axis of the link frame 110, and the required supporting force in accordance with the angle of the input/output device 60 in the up and down operation may realize the weight compensation according to the angle of the torsion spring 200a.

The link frame 110 may include a frame body 111 and at least one shaft coupling portion 112 extending from the frame body 111 to be coupled to the shaft 120.

The shaft coupling portion 112 may include a coupling portion body 113 and a through portion 114 provided on the coupling portion body 113 to insert the shaft 120.

A plurality of the shaft coupling portions 112 may be provided. Although the present disclosure exemplifies that four of the shaft coupling portions 112 extend from opposite sides of opposite ends of the frame body 111, but it is not limited thereto.

The first link frame 110a may include four of the shaft coupling portions 112 and the second link frame 110b may include four of the shaft coupling portions 112, and thus the link frame 110 according to the present disclosure may include a total of eight of the shaft coupling portions 112. However, the present disclosure is not limited thereto.

The through portion 114 may form a hole to allow the shaft 120 to pass therethrough, but is not limited thereto. The respective through portions 114 provided on two of the shaft coupling portions 112 facing each other among the plurality of shaft coupling portions 112 may be formed to be coaxial with each other.

The shaft 120 may include a shaft body 121 and a first coupling portion 122 formed so that the shaft 120 is coupled to the link frame 110 to be rotated together with the link frame 110.

The first coupling portion 122 may include a protrusion 122a protruding from the shaft body 121. The first coupling portion 122 may protrude from opposite sides of the shaft body 121.

A plurality of the first coupling portions 122 may be provided. Four of the first coupling portions 122 protruding from the opposite sides of opposite ends of the shaft body 121 may be provided. However, the present disclosure is not limited thereto.

The link frame 110 may include a second coupling portion 115 formed to be engaged with the first coupling portion 122 to be rotated together with the shaft 120. The second coupling portion 115 may extend from the through portion 114. The second coupling portion 115 may include a hole 115a, but is not limited thereto.

The actuator 200 may include a first end 210 supported by the shaft 120 and a second end 220 supported by the link frame 110. The first end 210 may be supported by the shaft 120 passing through the first link frame 110a, and the second end 220 may be supported by the second link frame 110b.

The first end 210 may be formed by winding the torsion spring 200a and may include a third coupling portion 211 provided to allow the actuator to be engaged with the shaft 120 and rotated together with the shaft 120.

The third coupling portion 211 may be formed by bending the first end 210 having a shape in which the torsion spring 200a is wound, but is not limited thereto.

The shaft 120 may include a fourth coupling portion 123 formed to be engaged with the third coupling portion 211 to be rotated together with the actuator 200. The fourth coupling portion 123 may extend from opposite ends of the shaft body 121.

The fourth coupling portion 123 may include a first supporting portion 124 extending from the shaft body 121 to support the actuator 200 and a groove 125 provided in the first supporting portion 124 to receive the third coupling portion 211.

The first supporting portion 124 may be inserted into the first end 210 on which the torsion spring 200a is wound. The third coupling portion 211 may be inserted into the groove 125. However, the present disclosure is not limited thereto.

The link frame 110 may include a second supporting portion 116 provided on the frame body 111 to support the second end 220. The second supporting portion 116 may protrude from the frame body 111.

The second supporting portion 116 may be formed in a cylindrical shape. The second end 220 may be formed by bending an end portion of the torsion spring 200a so as to be elastically supported on the second supporting portion 116. The bending of the second end 220 may correspond to the curvature of the second supporting portion 116. However, the present disclosure is not limited thereto.

Figure 6:
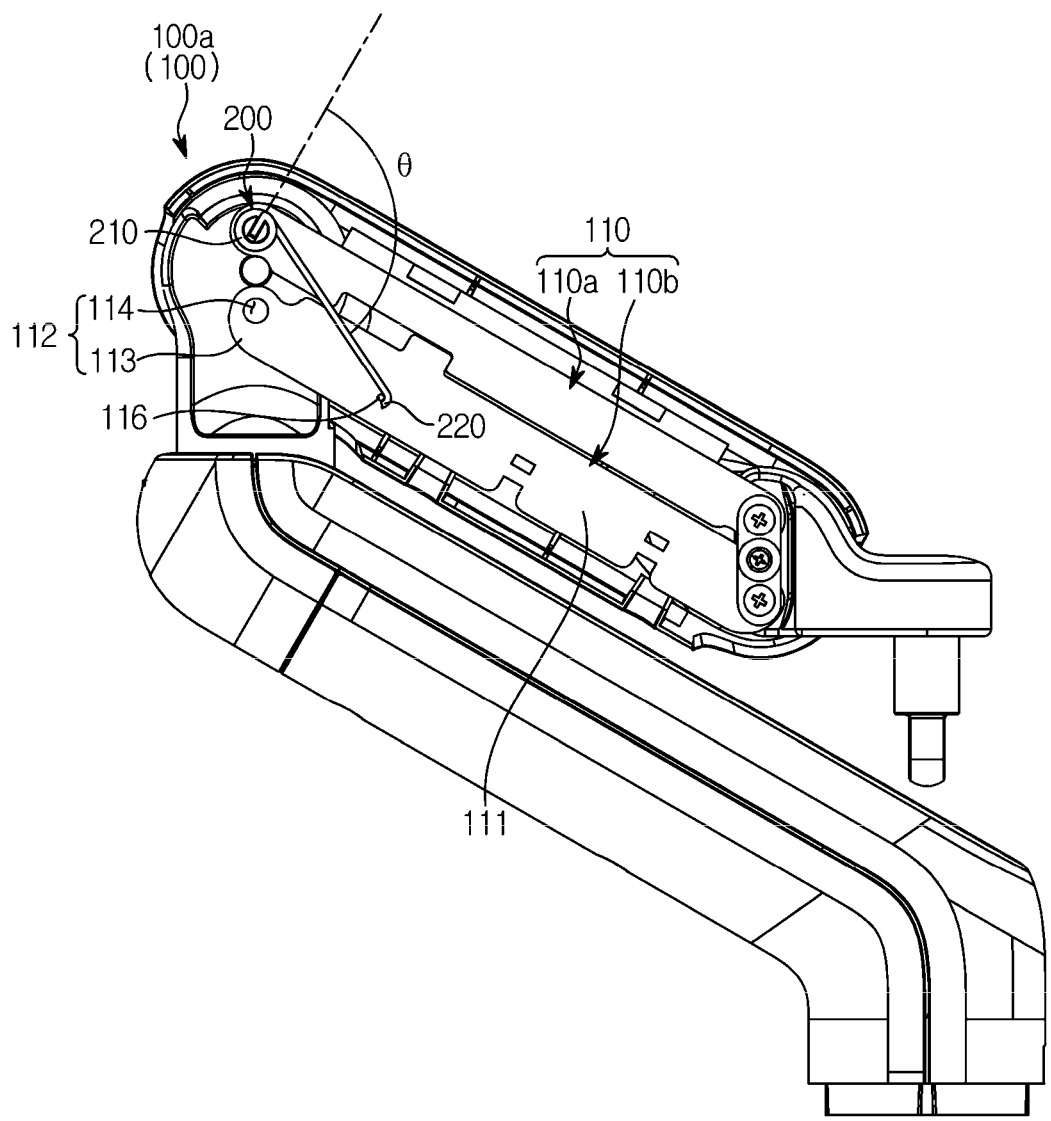
FIG. 6 is a view illustrating a state in which a connection device is moved to the lowermost portion in an ultrasonic diagnostic apparatus according to an embodiment of the present disclosure.
Figure 7:
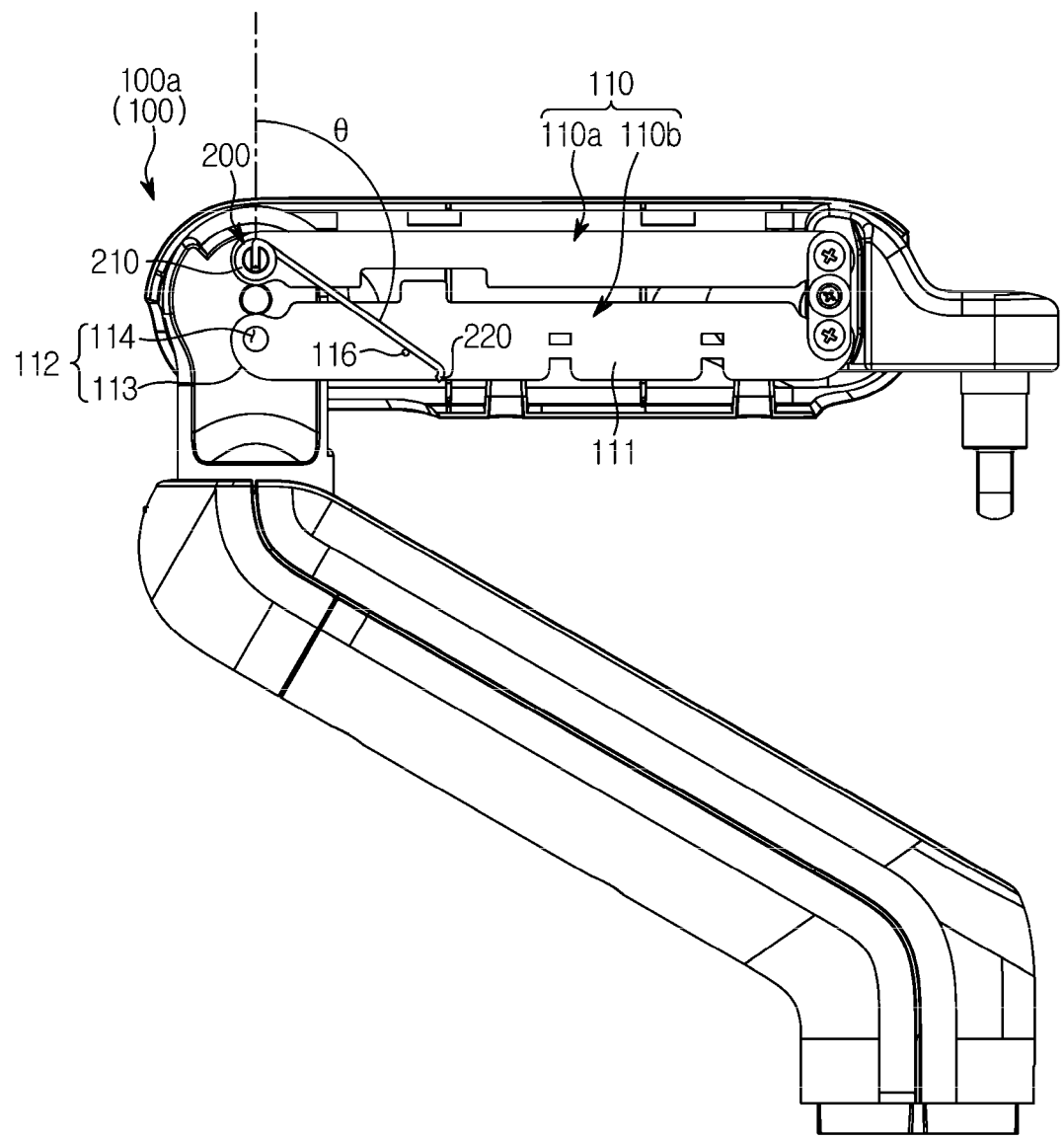
FIG. 7 is a view illustrating a state in which a connection device is moved to be horizontal in an ultrasonic diagnostic apparatus according to an embodiment of the present disclosure.
Figure 8:
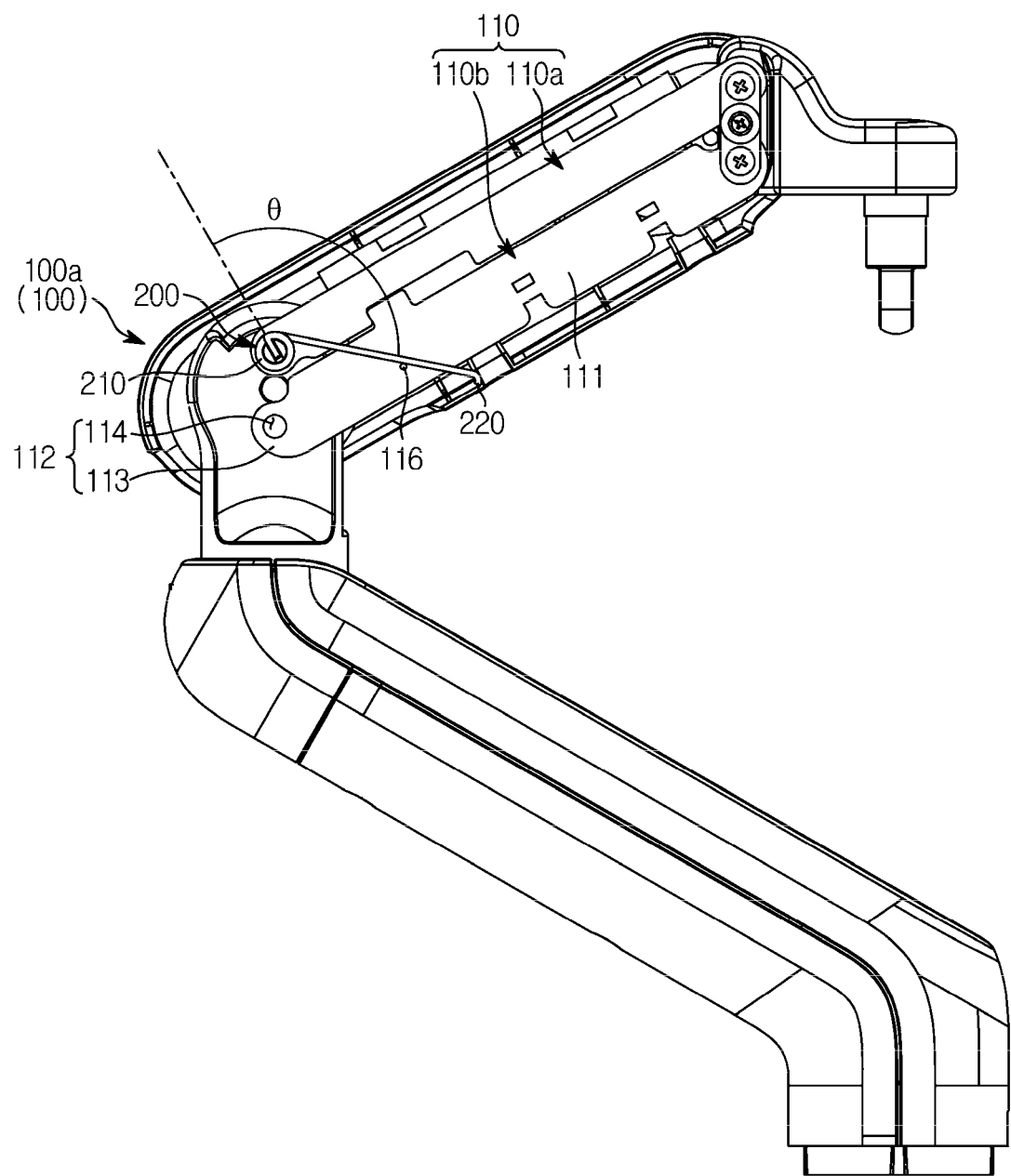
FIG. 8 is a view illustrating a state in which a connection device is moved to the uppermost portion in an ultrasonic diagnostic apparatus according to an embodiment of the present disclosure.

FIG. 6 is a view illustrating a state in which a connection device is moved to the lowermost portion in an ultrasonic diagnostic apparatus according to an embodiment of the present disclosure, FIG. 7 is a view illustrating a state in which a connection device is moved to be horizontal in an ultrasonic diagnostic apparatus according to an embodiment of the present disclosure, and FIG. 8 is a view illustrating a state in which a connection device is moved to the uppermost portion in an ultrasonic diagnostic apparatus according to an embodiment of the present disclosure.

As illustrated in FIGS. 6 to 8, the link frame 110 may be configured to be rotatable within a predetermined range about the shaft 120. The supporting force of the actuator 200 may vary depending on the weight of the input/output device 60 (refer to FIG. 1) and a rotation angle of the link frame 110.

For example, in a state where the link frame 110 is rotated upward (refer to FIG. 8), the rotation angle of the link frame 110 may be reduced as the link frame 110 rotates downward. Accordingly, the supporting force required for the weight compensation of the input/output device 60 may be increased. When the link frame 110 is horizontal (refer to FIG. 7), that is, when the rotation angle of the link frame 110 is right-angled, the required supporting force may be maximized.

As the link frame 110 is further rotated downward from the horizontal position (refer to FIG. 6), the supporting force required for the weight compensation of the input/output device 60 may be reduced.

Generally, an elastic force generated by the torsion spring 200a may have a substantially linear characteristic. Accordingly, in a case where a torsion spring having a fixed rotation axis is used as the actuator 200 for the weight compensation of the input/output device 60, the torsion spring may be used accurately only within a range in which the rotation angle of the link frame 110 is between 60 degrees and 90 degrees, which is an approximate proportional section.

However, in the case of applying the torsion spring 200a in which the rotation angle of the link frame 110 is set between 60 degrees and 90 degrees, a compensating supporting force greater than the required supporting force due to the linearity of the torsion spring 200a may be generated in the range of the rotation angle of the link frame 110 from 90 degrees to 120 degrees.

Accordingly, in this case, the input/output device 60 may not be maintained at the rotational angle of 120 degrees, and may be returned and positioned near the rotational angle of 90 degrees.

That is, in a case where a torsion spring having a fixed rotation axis is used, when the rotational angle of the link frame 110 is 90 degrees, perfect weight compensation may be realized, but when the rotation angle of the link frame 110 is in the range of 90 degrees to 120 degrees, the reaction force in the opposite direction of gravity is increased, and thus the link frame 110 may not be lowered to a position corresponding to the rotation angle of 120 degrees and may be positioned near a position corresponding to the rotation angle of 90 degrees.

The actuator 200 according to the present disclosure may include the torsion spring 200a having a rotation axis that is rotated together with the link frame 110 and the shaft 120.

Accordingly, the actuator 200 may exert the same rotational force irrespective of the rotation angle of the link frame 110. That is, since the rotation axis of the torsion spring 200a rotates together with the rotation of the link frame 110, an angle θ between a reference line and the torsion spring 200a may always be constant.

Contrary to the general case of using a torsion spring in which a rotation axis is fixed, since the rotation axis of the torsion spring 200a according to the present disclosure rotates together with the rotation of the link frame 110, the same supporting force may be generated without depending on the rotation angle of the link frame 110.

To this end, the shaft 120 of the present disclosure may be configured to be rotated together with the link frame 110 by engaging with the link frame 110, and the actuator 200 including the torsion spring 200a may be configured to be rotated together with the shaft 120 by engaging with the shaft 120.

The second supporting portion 116 may support the second end 220 and a portion between the first end 210 and the second end 220 according to the rotation of the link frame 110. That is, when the rotation angle of the link frame 110 is 120 degrees, the second supporting portion 116 may support the second end 220.

When the link frame 110 rotates upward so that the rotation angle of the link frame 110 is shifted from 120 degrees to 60 degrees, the second supporting portion 116 may support the portion between the first end 210 and the second end 220 toward the first end 210.

This is because the rotation axis of the first link frame 110a through which the shaft 120 supporting the first end 210 of the actuator 200 passes and the rotation axis of the second link frame 220b supporting the second end 220 of the actuator 200 are different from each other.

Figure 9:
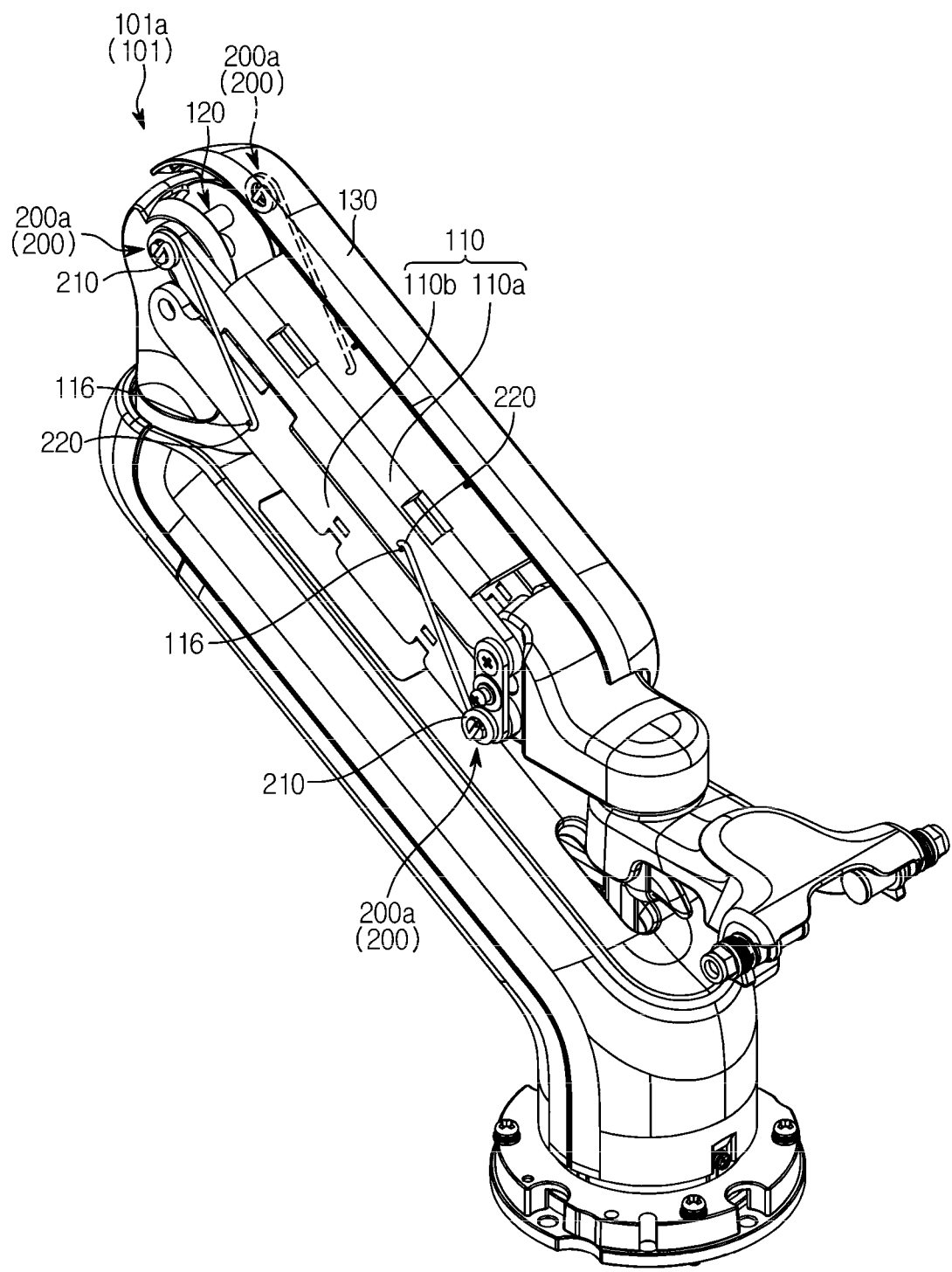
FIG. 9 is a perspective view illustrating the inside of a connection device in an ultrasonic diagnostic apparatus according to another embodiment of the present disclosure.

FIG. 9 is a perspective view illustrating the inside of a connection device in an ultrasonic diagnostic apparatus according to another embodiment of the present disclosure. As illustrated in FIG. 9, a connection device 101 according to another embodiment of the present disclosure may include an arm 101a for connecting the control panel 50 (refer to FIG. 1) and the display 40 (refer to FIG. 1).

A plurality of the actuators 200 provided on the arm 101a may be provided. The configurations of the connection device 101 according to another embodiment of the present disclosure may be the same as those of the connection device 100 according to an embodiment of the present disclosure except that the plurality of actuators 200 are provided.

Therefore, the same reference numerals and description as those of the connection device 100 according to an embodiment of the present disclosure may be omitted.

The plurality of actuators 200 may be disposed at opposite ends of the shaft 120, respectively. Since the link frame 110 according to the present disclosure may include eight of the shaft coupling portions 112 in total, eight of the actuators 200 in total may be provided.

That is, the plurality of actuators 200 may be disposed on a plurality of the respective shafts 120 inserted into the two of the respective shaft coupling portions 112 facing each other among the plurality of shaft coupling portions 112. However, the present disclosure is not limited thereto.

The number and positions of the plurality of actuators 200 may be appropriately selected so that the actuator 200 increases or decreases the supporting force for weight compensation of the input/output device 60 (refer to FIG. 1).

For example, the actuators 200 positioned at an upper portion in FIG. 9 may be disposed on opposite sides of the shaft 120 to generate supporting forces in the same direction to each other, and this may increase the supporting force for compensating for the weight of the input/output device 60.

The actuators 200 positioned at a lower portion in FIG. 9 may be disposed to generate supporting forces in opposite directions to each other, and this may decrease the supporting force for compensating for the weight of the input/output device 60.

In this case, although the magnitude of the user's force for moving the input/output device 60 may be increased, the operation performance of the input/output device 60 may be improved when the rotation angle of the link frame 110 is about 120 degrees.

Figure 10:
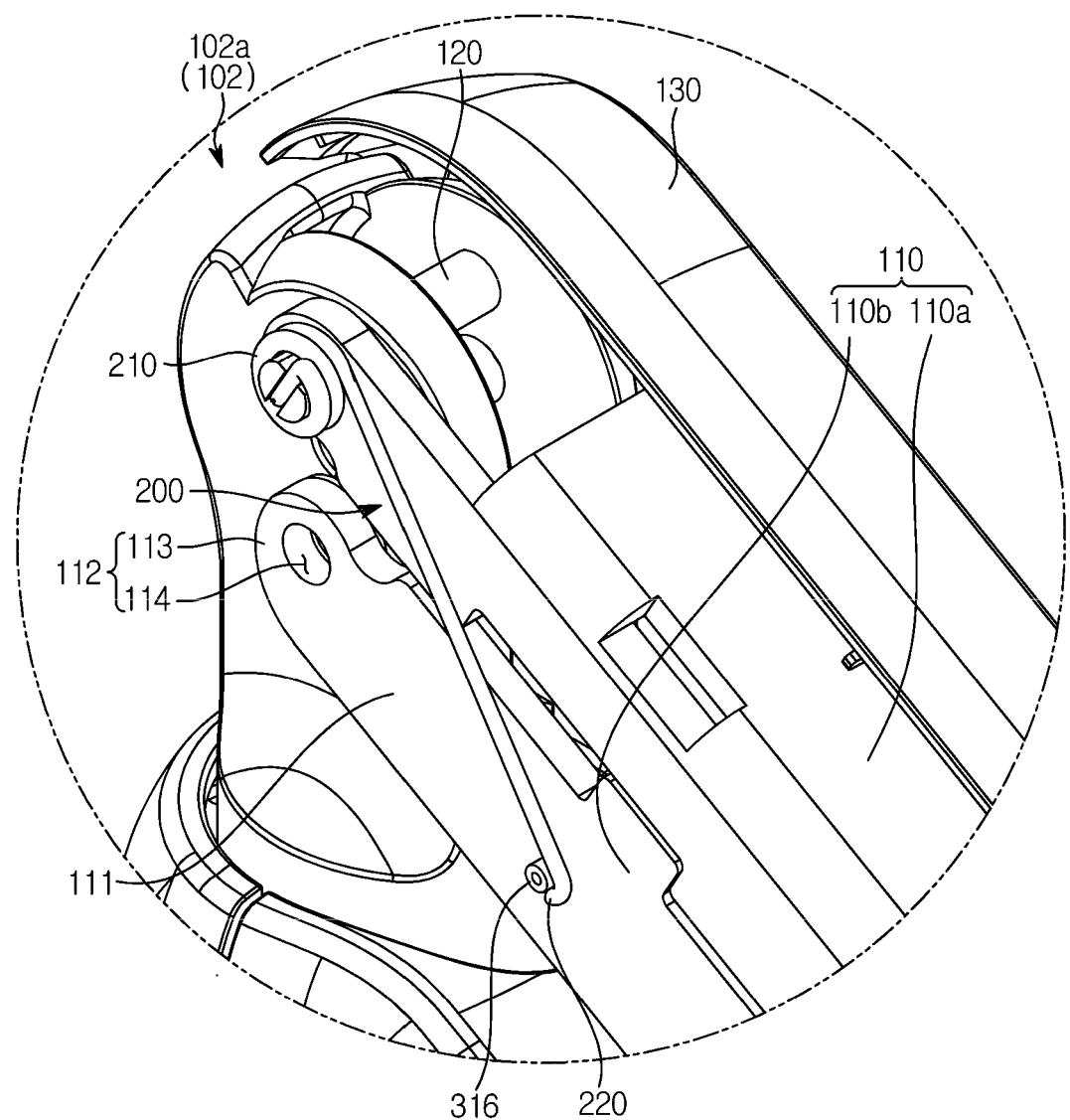
FIG. 10 is a view illustrating a state in which a second supporting portion includes a roller in an ultrasonic diagnostic apparatus according to another embodiment of the present disclosure.

FIG. 10 is a view illustrating a state in which a second supporting portion includes a roller in an ultrasonic diagnostic apparatus according to another embodiment of the present disclosure. As illustrated in FIG. 10, a connection device 102 according to another embodiment of the present disclosure may include an arm 102a for connecting the control panel 50 (refer to FIG. 1) and the display 40 (refer to FIG. 1).

The actuator 200 provided on the arm 102a may include a roller 316. The roller 316 may be provided to roll along the actuator 200 by the rotation of the link frame 110.

The configurations of the connection device 102 according to another embodiment of the present disclosure may be the same as those of the connection device 100 according to an embodiment of the present disclosure except that the second supporting portion 116 (refer to FIG. 5) of the connection device 100 according to an embodiment of the present disclosure is configured as the roller 316.

Therefore, the same reference numerals and description as those of the connection device 100 according to an embodiment of the present disclosure may be omitted.

As the second supporting portion 116 is configured as the rollers 316, the roller 316 may move more frictionlessly between the first end 210 and the second end 220 of the actuator 200 and support the actuator 200.

Meanwhile, although not shown in the drawings, the connection device 102 may include a friction bearing (not shown) that may reduce the frictional force between the link frame 110, the shaft 120, and the actuator 200 to smoothly rotate the link frame 110, the shaft 120, and the actuator 200.

Figure 11:
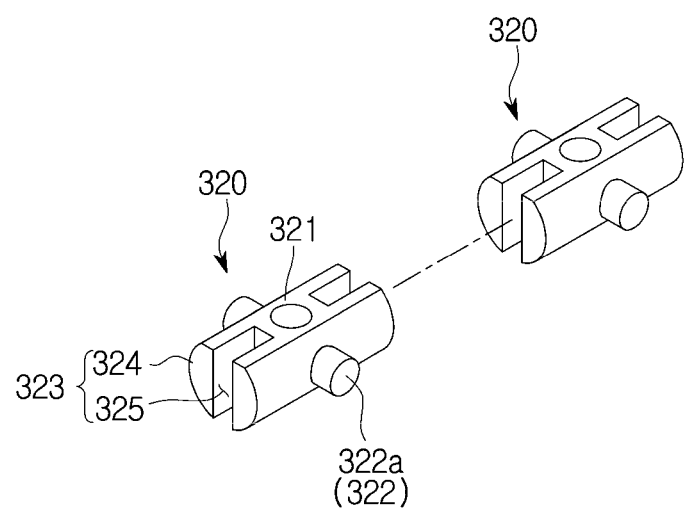
FIG. 11 is a view illustrating a plurality of shafts in an ultrasonic diagnostic apparatus according to another embodiment of the present disclosure.

FIG. 11 is a view illustrating a plurality of shafts in an ultrasonic diagnostic apparatus according to another embodiment of the present disclosure. As illustrated in FIG. 11, a plurality of shafts 320 according to another embodiment of the present disclosure may be provided.

The plurality of shafts 320 may be disposed on the plurality of shaft coupling portions 112 (refer to FIG. 5), respectively. The configurations of a connection device according to another embodiment of the present disclosure may be the same as those of the connection device 100 according to an embodiment of the present disclosure except that the plurality of shafts 320 are provided.

Therefore, the same reference numerals and description as those of the connection device 100 according to an embodiment of the present disclosure may be omitted.

The shaft 320 may include a shaft body 321 and a first coupling portion 322 configured such that the shaft 320 is engaged with the link frame 110 (refer to FIG. 5) and rotates together with the link frame 110.

The first coupling portion 322 may include a protrusion 322a protruding from the shaft body 321, The first coupling portion 322 may protrude from opposite sides of the shaft body 321.

A plurality of the first coupling portions 322 may be provided. For example, two of the first coupling portions 322 protruding from the opposite sides of the shaft body 321 may be provided. However, the present disclosure is not limited thereto.

The shaft 320 may include a fourth coupling portion 323 configured to be engaged with the third coupling portion 211 to be rotated together with the actuator 200 (refer to FIG. 5). The fourth coupling portion 323 may extend from opposite ends of the shaft body 321.

The fourth coupling portion 323 may include a first supporting portion 324 extending from the shaft body 321 to support the actuator 200 and a groove 325 provided on the first supporting portion 324 to receive the third coupling portion 211.

The first supporting portion 324 may be inserted into the first end 210 formed by winding the torsion spring 200a (refer to FIG. 5). The third coupling portion 211 may be inserted into the groove 325, but the present disclosure is not limited thereto.

The shaft 320 according to another embodiment of the present disclosure may be coupled to two of the shaft coupling portions 112 facing each other among the plurality of shaft coupling portions 112, respectively. Therefore, the actuator 200 coupled to the shaft 320 may be disposed not only outside the link frame 110 refer to FIG. 5) but also inside the link frame 110.

Accordingly, since the link frame 110 according to the present disclosure may include eight of the shaft coupling portions 112 in total, sixteen of the actuators 200 in total may be disposed outside and inside the link frame 110.

That is, the plurality of actuators 200 may be appropriately disposed on the required positions among sixteen of the fourth coupling portions 323. However, the present disclosure is not limited thereto.

As is apparent from the above, the user can smoothly move an input/output device because the present disclosure includes an improved actuator for compensating for the weight of the input/output device.

Defects of an ultrasonic diagnostic apparatus can be minimized because the present disclosure includes an improved actuator including a torsion spring.

The force required when the user moves a connection device can be minimized because the present disclosure includes an improved actuator to exert the same rotational force regardless of the rotation angle of the connection device.

Although a few embodiments of the present disclosure have been shown and described, it would be appreciated by those skilled in the art that changes may be made in these embodiments without departing from the principles and spirit of the present disclosure in the scope of which is defined in the claims and their equivalents.

What is claimed is:

1. An ultrasonic diagnostic apparatus comprising:
a main body;
an input/output device coupled to the main body and configured to receive information from a user or output information received from the main body; and
a connection device to connect the main body and the input/output device,
wherein the connection device includes:
a shaft having a shaft body;
a link frame having a frame body and a shaft coupling portion extending from the frame body to be coupled with the shaft, wherein the link frame is configured to be rotatable about the shaft in a first direction; and
an actuator including a torsion spring having a rotation axis that is rotated together with the link frame and the shaft in the first direction,
wherein the torsion spring has a first end having a coupling portion wound around the shaft and engaged with the shaft and a second end provided to be movable with respect to the link frame,
wherein the entire torsion spring rotates according to the rotation of the link frame to keep a torsion angle of the torsion spring constant, and
wherein the link frame includes a first link frame and a second link frame adjacent to the first link frame, and the first end of the torsion spring is fixed to the shaft passing through the first link frame and the second end of the torsion spring is supported by the second link frame.

2. The ultrasonic diagnostic apparatus according to claim 1, wherein:
the actuator is configured to exert the same rotational force irrespective of a rotation angle of the link frame.

3. The ultrasonic diagnostic apparatus according to claim 1, wherein:
the shaft includes a first coupling portion provided to be engaged with the link frame and rotated together with the link frame, and
the link frame includes a second coupling portion provided to be engaged with the first coupling portion.

4. The ultrasonic diagnostic apparatus according to claim 1, wherein:
the coupling portion of the actuator is a third coupling portion,
wherein the third coupling portion is rotated together with the shaft, and
the shaft includes a fourth coupling portion provided to be engaged with the third coupling portion.

5. The ultrasonic diagnostic apparatus according to claim 3, wherein:
the first coupling portion includes a protrusion protruding from the shaft body.

6. The ultrasonic diagnostic apparatus according to claim 5, wherein:
the shaft coupling portion includes a coupling portion body and a through portion provided on the coupling portion body to insert the shaft body, and
the second coupling portion includes a hole extending from the through portion.

7. The ultrasonic diagnostic apparatus according to claim 4, wherein:
the fourth coupling portion includes a first supporting portion extending from the shaft body to support the actuator, and a groove provided on the first supporting portion to receive the third coupling portion.

8. The ultrasonic diagnostic apparatus according to claim 1, wherein:
the link frame further includes a second supporting portion provided on the frame body to support the second end.

9. The ultrasonic diagnostic apparatus according to claim 8, wherein:
the second supporting portion supports the second end and a portion between the first end and the second end according to the rotation of the link frame.

10. The ultrasonic diagnostic apparatus according to claim 8, wherein:
the second supporting portion includes a roller provided to roll along the actuator by the rotation of the link frame.

11. The ultrasonic diagnostic apparatus according to claim 1, wherein:
a plurality of the actuators are provided, and
the plurality of actuators are disposed at opposite end portions of the shaft, respectively.

12. The ultrasonic diagnostic apparatus according to claim 6, wherein:
a plurality of the shafts, the shaft coupling portions, and the actuators are provided, and
the plurality of actuators are disposed on the plurality of respective shafts inserted into two of the respective shaft coupling portions facing each other among the plurality of shaft coupling portions.

13. The ultrasonic diagnostic apparatus according to claim 6, wherein:
a plurality of the shafts and the shaft coupling portions are provided, and
the plurality of shafts are disposed on the plurality of shaft coupling portions, respectively.

14. An ultrasonic diagnostic apparatus comprising:
a main body;
an input/output device coupled to the main body and configured to receive information from a user or output information received from the main body; and
a connection device to connect the main body and the input/output device,
wherein the connection device includes:
a link frame provided to be rotatable about the shaft in a first direction;
a shaft coupled with one end portion of the link frame to be rotated together with the link frame; and
an actuator having a rotation axis that is rotated together with the link frame and the shaft in the first direction,
wherein the actuator has a first end having a coupling portion wound around the shaft and engaged with the shaft and a second end provided to be movable with respect to the link frame,
wherein the entire actuator rotates according to the rotation of the link frame to keep a torsion angle of the actuator constant, and
wherein the link frame includes a first link frame and a second link frame adjacent to the first link frame, and the first end of the actuator is fixed to the shaft passing through the first link frame and the second end of the actuator is supported by the second link frame.

15. The ultrasonic diagnostic apparatus according to claim 14, wherein:
the actuator includes a torsion spring having the first end fixed to the shaft and the second end supported by the link frame.

* * * * *